US00PP18656P2

(12) United States Plant Patent
Van Zanten

(10) Patent No.: US PP18,656 P2
(45) Date of Patent: Mar. 25, 2008

(54) POINSETTIA PLANT NAMED 'ATN VP6'

(50) Latin Name: *Euphorbia pulcherrima*
Varietal Denomination: ATN VP6

(75) Inventor: Leo Van Zanten, Oxnard, CA (US)

(73) Assignee: Athena Mudas LTDA, Sao Jose do Rio Preto (BR)

( * ) Notice: Subject to any disclaimer, the term of this patent is extended or adjusted under 35 U.S.C. 154(b) by 0 days.

(21) Appl. No.: 11/495,827

(22) Filed: Jul. 28, 2006

(51) Int. Cl.
*A01H 5/00* (2006.01)

(52) U.S. Cl. ..... Plt./306
(58) Field of Classification Search ..... Plt./306, Plt./303
See application file for complete search history.

(56) References Cited

U.S. PATENT DOCUMENTS

PP11,869 P2 * 5/2001 Fruehwirth ..... Plt./306

OTHER PUBLICATIONS

Broertjes et al. "Application of Mutation Breeding Methods in the improvement of Vegetatively Propagated Crops," Elsevier Scientific Publishing Company, 1978, pp. 12–13 and 118–119. (3 pages total).*

* cited by examiner

*Primary Examiner*—Kent Bell
*Assistant Examiner*—S. B. McCormick-Ewoldt

(57) ABSTRACT

A new and distinct Poinsettia plant cultivar is disclosed, characterized by medium-sized, rose pink bracts, blooming consistently after 7.5 weeks of night-length of 13.5 hours or more, with a post-production longevity of 6 weeks or more.

1 Drawing Sheet

Latin name of the genus and species: *Euphorbia pulcherrima.*
Variety denomination: 'ATN VP6'.

BACKGROUND OF THE INVENTION

The new cultivar 'ATN VP6' is a product of a planned breeding program. The new variety was discovered as a whole plant induced mutation from the original cultivar 'ATN VR2' (U.S. Plant Pat. No. 17,522). The original cuttings were treated in February 2004 with gamma rays at 25 Gy. The new cultivar was discovered and selected by Leo van Zanten in November 2005.

Asexual reproduction of the new cultivar 'ATN VP6' by terminal cuttings was performed in Oxnard, Calif., USA and has shown that the unique features of this new cultivar are stable and reproduced true to type on successive generations.

SUMMARY OF THE INVENTION

The cultivar 'ATN VP6' has not been observed under all possible environmental conditions. The phenotype may vary somewhat with variations in environment such as temperature, daylength, and light intensity, without, however, any variance in genotype.

The following traits have been repeatedly observed and are determined to be basic characteristics of 'ATN VP6' which in combination distinguish this Poinsettia as a new and distinct cultivar:

1. Rose pink bract color;
2. Medium sized bracts in tight and flat rosette-like arrangement;
3. Dark-green foliage with moderate lobes;

4. Bracts are medium-sized, v-shaped with the branches slanting upright;
5. Begin of flowering after 7.5 weeks of night-length of 13.5 hours or more and;
6. Post production longevity of 6 weeks or more.

Plants of the new cultivar, 'ATN VP6' are similar to plants of the parent variety 'ATN VR2' in most horticulture characteristics, however plants of the new cultivar 'ATN VP6' have a wider plant spread. In addition, the new variety 'ATN VP6' has pink bracts compared to the red bracts of the parent variety. Finally, the bracts of 'ATN VP6' are longer and wider than the bracts of the parent variety 'ATN VR2'.

In comparison to the commercially available variety 'Festival Pink' (U.S. Plant Pat. No. 14,559), 'ATN VP6' has different color pink bracts as well as different color green foliage. The new variety 'ATN VP6' is taller than 'Festival Pink'. Finally, the comparable variety 'Festival Pink' has more bracts per inflorescence than the new cultivar 'ATN VP6'.

In comparison to the commercially available variety '490 Pink' (U.S. Plant Pat. No. 8,817), 'ATN VP6' has shorter bracts than the comparable variety. The comparable variety '490 Pink' has different color pink bracts and more bracts per inflorescence. Finally, the comparable variety is shorter but wider in overall plant size than 'ATN VP6'.

BRIEF DESCRIPTION OF THE PHOTOGRAPH

The accompanying photograph in FIG. 1 illustrates in full color a typical plant of 'ATN VP6' grown in a 6.5-inch pot. One cutting was used in the pot, planted in late August and grown in a greenhouse using approximately 4,000-foot candles of light. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'ATN VP6' plants grown in Oxnard, Ventura County, Calif., from late August to late November of 2004. The plants are approximately 126 days old. The growing temperature ranged from 18° C. to 20° C. at night to 20° C. to 24° C. during the day.

Botanical classification: *Euphorbia pulcherrima* cultivar 'ATN VP6'.
Commercial classification: Poinsettia.

PROPAGATION

Time to initiate rooting: Approximately 10 days at 20-22° C.
Time to develop roots: Sufficiently rooted for transplanting after about 25 days in a greenhouse at temperature of 20-22° C.

PLANT

Form: Mounding inverted triangle self-branching, mounded top of plant.
Growth habit: Moderately compact structure, pinched plants are bushy with the branches upright directed at an angle of roughly 35 degrees, foliage canopy uniformly rounded.
Height: In 6.5 inch pot, approximately 38 cm.
Plant spread: In 6.5 inch pot, approximately 42 cm.
Growth rate: Low to medium vigor.
Branching characteristics: Free-branching.
Diameter of branches: Approximately 0.7 cm.
Average number of branches: Approximately 7 after pinching.
Length of lateral branches: Approximately 25 cm.
Number of leaves per lateral branch: Approximately 7.
Stem color: Near Green 143C.
Age of plant described: Approximately 126 days.

FOLIAGE

Leaf:
- *Arrangement.*—Alternate single.
- *Average length.*—Approximately 12 cm.
- *Average width.*—Approximately 8 cm.
- *Shape of blade.*—Ovate.
- *Lobes.*—Moderate lobes.
- *Tip.*—Acuminate.
- *Base.*—Rounded to almost truncate.
- *Attachment.*—Stalked.
- *Margin.*—Entire, apart from the lobes.
- *Aspect.*—Slightly recurved.
- *Texture of top surface.*—Glabrous.
- *Texture of bottom surface.*—Glabrous.
- *Leaf internode length.*—About 2.5 cm.
- *Color.*—Young foliage upper side: Near Yellow-Green 147A. Young foliage under side: Near Green 137B. Mature foliage upper side: Near Green 137A. Mature foliage under side: Near Green 138B.
- *Venation.*—Type: Pinnate. Venation color upper side: Near Green 143C with near Greyed-Red 182B pigment at base. Venation color under side: Near Green 143D.

Petiole:
- *Average length.*—Approximately 6 cm.
- *Color.*—Near Greyed-Red 182B.
- *Diameter.*—Approximately 0.3 cm.
- *Texture.*—Smooth.
- *Aspect.*—Petioles are horizontally directed.

FLOWER

Inflorescence:
- *Inflorescence description.*—Inflorescences are compound corymbs of cyathia with colored flower bracts subtending the cyathia.
- *Blooming habit.*—Begin under natural short day conditions in the fall: Botanically (cyathia open) in late December. Commercially (bracts colored, marketable in late November).
- *Flowering response time.*—60 days after beginning of short days (nights longer than 13.5 hours.)
- *Flowering description.*—Whole inflorescence with surrounding bracts. About medium-size, star-shaped, with the bracts directed in a tight arrangement and overlapping.
- *Natural flowering season.*—Mainly from late November to late December.
- *Number of inflorescences per lateral branch.*—Approximately 1.
- *Diameter of inflorescence.*—Approximately 12 cm.
- *Height of inflorescence.*—Approximately 7.6 cm.
- *Number of bracts per inflorescence.*—About 14.
- *Persistence.*—Persistent.

Bracts:
- *Length of largest bracts.*—About 13 cm.
- *Width of largest bracts.*—About 12 cm.
- *Keeping quality.*—Plants have a post-production longevity of 6 weeks.
- *Shape.*—Ovate, with moderate lobes.
- *Base.*—Obtuse, moderate lobes with acute tips.
- *Terminal tip.*—Acuminate.

Texture:
- *Upper surface.*—Glabrous, velvety.
- *Lower surface.*—Glabrous velvety.
- *Aspect.*—Slightly recurved.
- *Venation pattern.*—Pinnate.

Color:
- *Developing bracts.*—Upper surface: Near Red 50B. Lower surface: Near Red 50C.
- *Mature bracts.*—Upper surface: Near Red 51B. Lower Surface: Near Red 51B.

Bract petiole:
- *Length.*—Approximately 4 cm.
- *Diameter.*—Approximately 0.3 cm.
- *Color.*—Near Red 53C.

Cyathium: About 12 per corymb.
Diameter of cyathia cluster: About 3.2 cm.
Length of individual cyathia: Approximately 1.2 cm.
Width of individual cyathia: Approximately 0.6 cm.
Shape: Ovoid.
Color:
- *Immature.*—Near Yellow 9B.
- *Mature.*—Near Yellow-Orange 15A.

Aging: Near Yellow-Green 145A.
Nectar cups/nectaries:
- *Quantity.*—One or two per cyathium.
- *Width.*—Up to 5 mm wide.
- *Color.*—Near Yellow 9A.

Peduncle:
- *Length.*—About 0.3 cm.
- *Diameter.*—About 0.2 cm.
- *Strength.*—Strong.
- *Aspect.*—Upright.

*Texture.*—Glabrous.

*Color.*—Near Yellow-Green 145B.

Reproductive organs:

*Stamens.*—Approximately 15 in a cluster.

*Anther shape.*—Bi-lobed.

*Anther length.*—About 0.1 cm.

*Anther color.*—Near Red 51A.

*Quantity of pollen.*—Moderate.

*Pollen color.*—Near Yellow-Orange 16A.

Pistils: None observed.

OTHER CHARACTERISTICS

Disease resistance: No resistance nor susceptibility has been observed to normal pests and diseases of poinsettia crops.

Fruit/seed production: No seed observed.

What is claimed is:

1. A new and distinct cultivar of Poinsettia plant named 'ATN VP6' as herein illustrated and described.

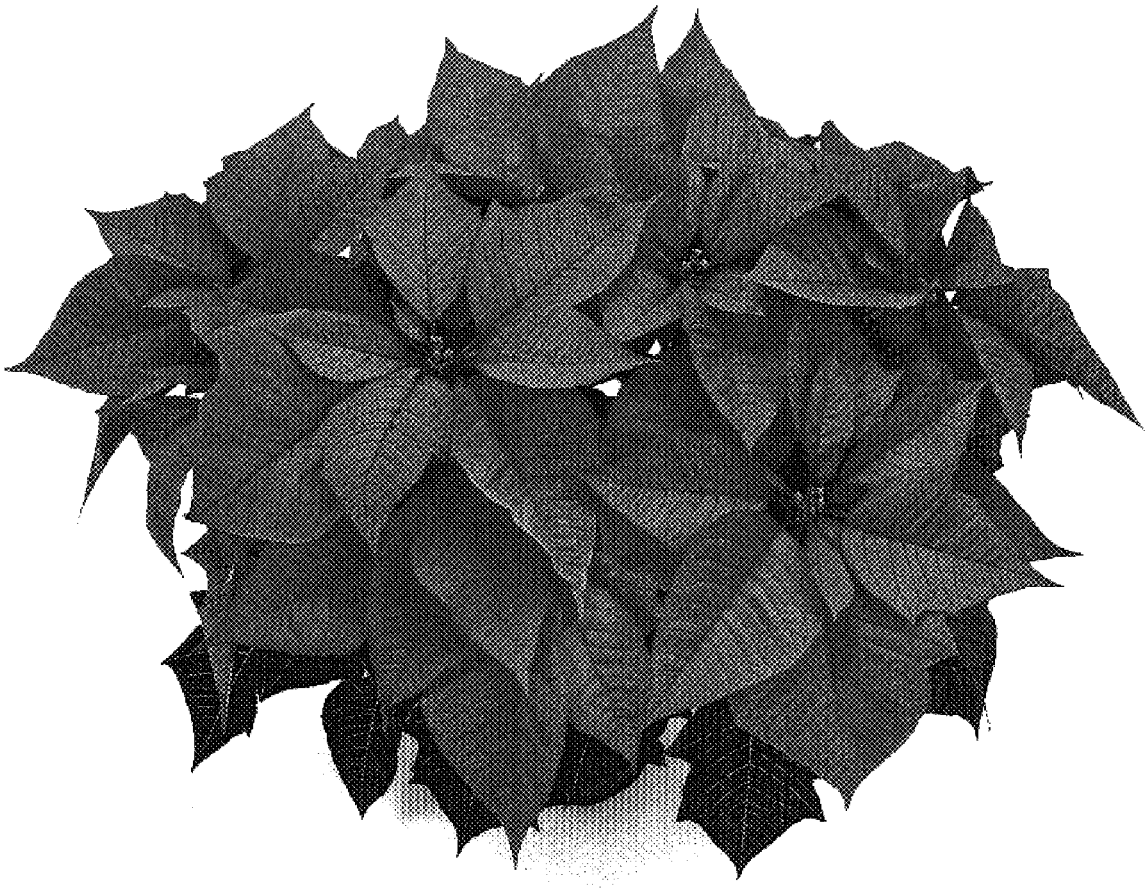

* * * * *